(12) United States Patent
Najafi et al.

(10) Patent No.: US 12,402,809 B2
(45) Date of Patent: Sep. 2, 2025

(54) DETECTING FRAILTY AND FOOT AT RISK USING LOWER EXTREMITY MOTOR PERFORMANCE SCREENING

(71) Applicant: Baylor College of Medicine, Houston, TX (US)

(72) Inventors: Bijan Najafi, Houston, TX (US); Hadi Rahemi, Houston, TX (US); Hyoki Lee, Houston, TX (US); Hung Nguyen, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 915 days.

(21) Appl. No.: 17/052,611

(22) PCT Filed: May 2, 2019

(86) PCT No.: PCT/US2019/030405
§ 371 (c)(1),
(2) Date: Nov. 3, 2020

(87) PCT Pub. No.: WO2019/213399
PCT Pub. Date: Nov. 7, 2019

(65) Prior Publication Data
US 2021/0236021 A1 Aug. 5, 2021

Related U.S. Application Data

(60) Provisional application No. 62/670,715, filed on May 11, 2018, provisional application No. 62/667,403, filed on May 4, 2018.

(51) Int. Cl.
*A61B 5/11* (2006.01)
*A61B 5/00* (2006.01)
(Continued)

(52) U.S. Cl.
CPC ............ *A61B 5/112* (2013.01); *A61B 5/0004* (2013.01); *A61B 5/6807* (2013.01);
(Continued)

(58) Field of Classification Search
CPC .............................. A61B 5/112; A61B 5/7275
See application file for complete search history.

(56) References Cited

U.S. PATENT DOCUMENTS

2008/0045804 A1 2/2008 Williams
2010/0049095 A1* 2/2010 Bunn ...................... G16H 40/60
600/595

(Continued)

FOREIGN PATENT DOCUMENTS

CN 106821680 A * 6/2017 ........... A61B 5/1038

OTHER PUBLICATIONS

Muro-de-la-Herran, A.; et. al., Gait Analysis Methods: An Overview of Wearable and Non-Wearable Systems, Highlighting Clinical Applications, 2014, Sensors, 14, 3362-3394. (Year: 2014).*

(Continued)

*Primary Examiner* — Benjamin S Melhus
(74) *Attorney, Agent, or Firm* — Norton Rose Fulbright US LLP

(57) ABSTRACT

Lower extremity motion data may be received from one or more sensors. The lower extremity motion data may be used to quantify propulsion performance, which is used to calculate one or more gait characteristics of the lower extremity. A risk level of the lower extremity may be determined based, at least in part, on the calculated gait characteristics.

20 Claims, 7 Drawing Sheets

(51) Int. Cl.
*G06N 3/00* (2023.01)
*G06N 3/008* (2023.01)
*G06N 3/04* (2023.01)
*G16H 40/67* (2018.01)
*G16H 50/30* (2018.01)

(52) U.S. Cl.
CPC .......... *A61B 5/7267* (2013.01); *A61B 5/7275* (2013.01); *G06N 3/008* (2013.01); *G06N 3/04* (2013.01); *G16H 40/67* (2018.01); *G16H 50/30* (2018.01)

(56) References Cited

U.S. PATENT DOCUMENTS

| | | | | |
|---|---|---|---|---|
| 2011/0288811 | A1* | 11/2011 | Greene | A61B 5/6275 |
| | | | | 702/141 |
| 2013/0110475 | A1 | 5/2013 | Greene et al. | |
| 2014/0336003 | A1* | 11/2014 | Franz | A61B 5/389 |
| | | | | 482/8 |
| 2015/0260514 | A1 | 9/2015 | Menelas et al. | |
| 2015/0272511 | A1* | 10/2015 | Najafi et al. | A61B 5/7275 |
| | | | | 600/301 |
| 2016/0029943 | A1* | 2/2016 | Mizuochi | A61B 5/0022 |
| | | | | 600/595 |
| 2016/0029954 | A1* | 2/2016 | Sato | A61B 5/681 |
| | | | | 702/145 |
| 2016/0030804 | A1* | 2/2016 | Mizuochi | A61B 5/11 |
| | | | | 482/8 |
| 2016/0030807 | A1* | 2/2016 | Matsumoto | A61B 5/11 |
| | | | | 600/595 |
| 2016/0030808 | A1* | 2/2016 | Uchida | G09B 19/0038 |
| | | | | 482/8 |
| 2016/0030823 | A1* | 2/2016 | Sato | G09B 19/0038 |
| | | | | 434/255 |
| 2016/0114213 | A1* | 4/2016 | Lee | A63B 24/0075 |
| | | | | 434/255 |
| 2016/0370854 | A1* | 12/2016 | Steele | G06F 3/011 |
| 2017/0127978 | A1* | 5/2017 | Suydam | A61B 5/7282 |
| 2017/0249821 | A1 | 8/2017 | Coleman Boone et al. | |
| 2017/0281085 | A1* | 10/2017 | Lee | A61B 5/1118 |
| 2018/0111021 | A1* | 4/2018 | Matsumoto | A63B 24/0006 |
| 2018/0220937 | A1* | 8/2018 | Mizuochi | A61B 5/112 |
| 2018/0221239 | A1* | 8/2018 | Kuchenbecker | A61H 3/008 |
| 2019/0150793 | A1* | 5/2019 | Barth | G06N 3/08 |

OTHER PUBLICATIONS

Shamaei, Kamran et al. "Estimation of quasi-stiffness and propulsive work of the human ankle in the stance phase of walking." PloS one vol. 8,3 (2013): e59935. doi:10.1371/journal.pone.0059935 (Year: 2013).*

* cited by examiner

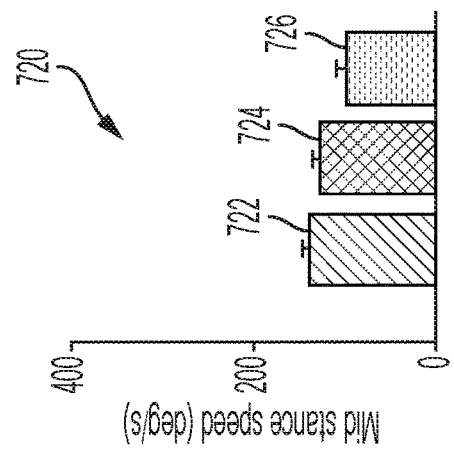
FIG. 7A
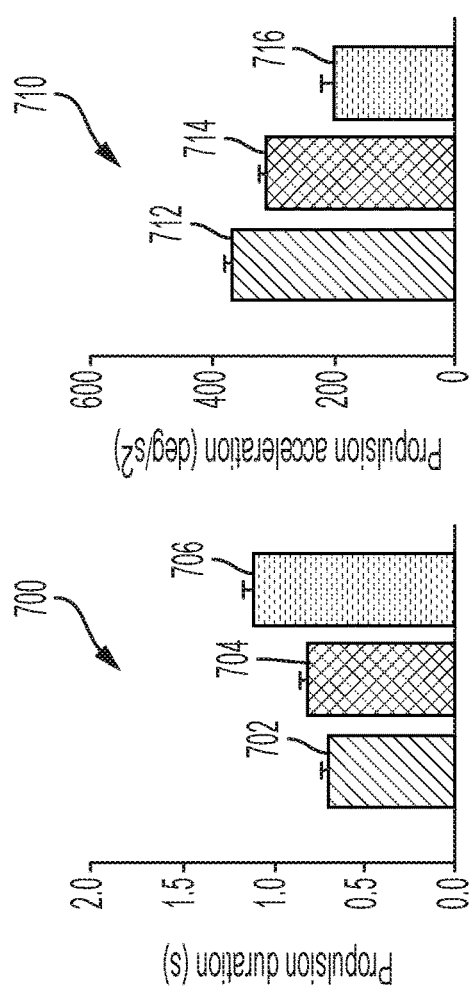
FIG. 7B
FIG. 7C
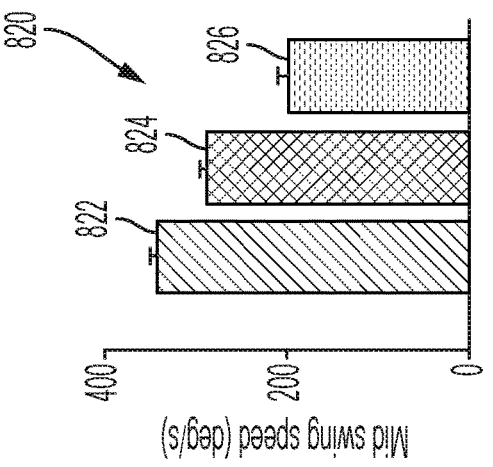
FIG. 8A
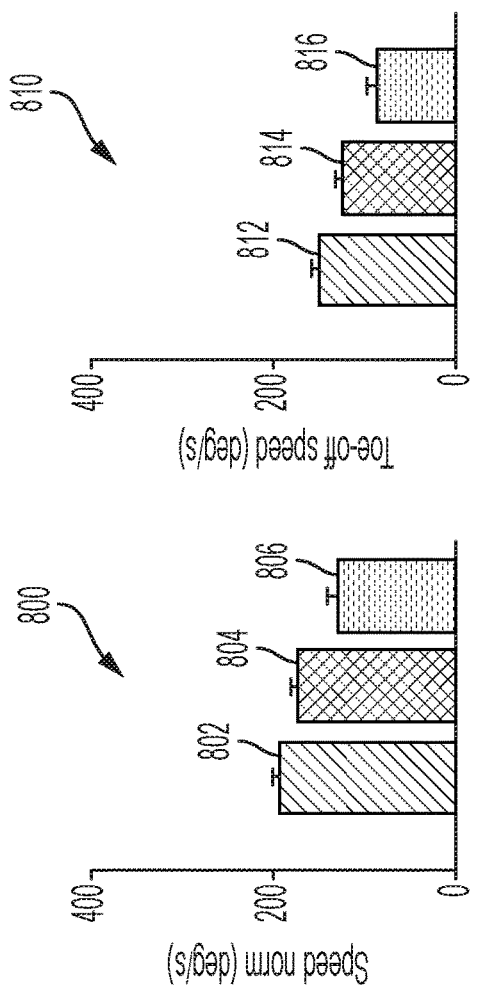
FIG. 8B
FIG. 8C

DETECTING FRAILTY AND FOOT AT RISK USING LOWER EXTREMITY MOTOR PERFORMANCE SCREENING

CROSS-REFERENCE TO RELATED APPLICATIONS

This application is a national phase application under 35 U.S.C. § 371 that claims priority to International Application No. PCT/US2019/030405 filed May 2, 2019, which claims priority to U.S. Provisional Patent Application Ser. No. 62/667,403 filed May 4, 2018, and also to U.S. Provisional Patent Application Ser. No. 62/670,715 filed May 11, 2018, all of which are incorporated herein by reference in their entirety.

GOVERNMENT LICENSE RIGHTS

This invention was made with government support under Grant #CA190933 awarded by the National Institutes of Health; Grant #AG050338 awarded by the National Institutes of Health; Grant #AG032748 awarded by the National Institutes of Health; and Grant #AG053108 awarded by the National Institutes of Health. The government has certain rights in the invention.

FIELD OF THE DISCLOSURE

The instant disclosure relates to medical diagnostics and intervention. More specifically, certain portions of this disclosure relate to a computerized platform for evaluating lower extremity risk based on motion data.

BACKGROUND

Lower extremity health is important to overall health and quality of life. Lower extremity problems, such as a foot or ankle problems, may reduce mobility and negatively impact an individual's overall health. Lower extremity problems are highly prevalent in older populations and increase the risk of falls, frailty, foot ulcers, foot deformity, and lower extremity amputation. For example, foot and/or ankle problems may reduce mobility, increase a likelihood of other injuries resulting from falls, and may, in extreme scenarios, require amputation, which may lead to additional medical complications.

As an individual ages, geriatric conditions and syndromes, such as frailty and/or poor motor performance, may appear and may affect lower extremity performance. Frailty, the loss in physiological reserves of an individual, is highly prevalent in older populations. Current frailty analysis techniques require the presence of trained personnel to observe and assess an individual's condition. As such, current frailty analysis techniques are often limited to supervised and controlled environments and cannot detect long-term changes over time, such as subtle progression in frailty stages. Additionally, treatment plans for lower extremity conditions, such as frailty, may have unpredictable impacts on lower extremity performance that are not observable using current techniques, outside of a controlled environment.

Shortcomings mentioned here are only representative and are included simply to highlight that a need exists for improved lower extremity performance analysis. Embodiments described herein address certain shortcomings, but not necessarily each and every shortcoming. Furthermore, embodiments described herein may present other benefits than, and be used in other applications than, those of the shortcomings described above.

SUMMARY

Motion data for a lower extremity may be used to determine a risk level of the lower extremity and/or an overall risk level for an individual. A sensor may sense motion of a lower extremity of a user and may transmit motion data to a processing station for analysis. The motion data may be analyzed to determine gait characteristics of the user, such as during a propulsion phase of walking and/or running. Gait characteristics related to propulsion efficiency may be used to determine a risk level of a lower extremity. Based on the analysis of user gait characteristics, a risk level or frailty of the lower extremity and/or the user may be determined. The risk level or frailty may be used to suggest treatments or adjustments to current treatments to avoid complications resulting from lower extremity maladies and/or to improve lower extremity functionality. Gait characteristics of the user may be stored and analyzed over long periods of time, such as hours, days, months, or years, and analyzed to detect subtle changes in user gait that may indicate health problems involving a lower extremity. The use of sensors to collect data over time for analysis allows for detection of lower extremity health problems outside of an observed controlled environment, which may allow for earlier detection and lower treatment costs. Furthermore, the collected data may be used to determine the success or failure of treatment plans.

Received motion data may be used to determine a risk level of a lower extremity. A method of processing motion data may begin with receiving motion data of a lower extremity of a user from one or more sensors. For example, one or more sensors may sense motion of a leg, ankle, and/or foot and may transmit motion data regarding motion of the leg, ankle, and/or foot to a processing station. The motion data may, for example, include kinematics (e.g., an angular velocity and/or acceleration) of a leg of a user collected using an accelerometer and/or gyroscope. One or more sensors may be integrated into a wearable device, such as a shoe, an angle foot orthosis, a sock, an insole, or an offloading. Alternatively, a sensor may be directly attached to a skin of a user via a strap, adhesive, or other attachment mechanism, or even implanted beneath a user's skin.

One or more gait characteristics may be calculated based, at least in part, on the received motion data. For example, a processing station may analyze received motion data of a lower extremity of a user to determine characteristics of movement of the lower extremity when walking and/or running. Calculating one or more gait characteristics may include identifying and quantifying a propulsion phase of movement of the lower extremity using propulsion phase characteristics. For example, a beginning and ending of a propulsion phase (example propulsion phase characteristics quantified using the motion data) may be determined based on motion data, and gait characteristics may be calculated based on motion data between the beginning and the end of the propulsion phase. Quantifying a propulsion phase may also include determining a duration of the propulsion phase (another example of a propulsion phase characteristic), by determining a time between the beginning of the propulsion phase and the end of the propulsion phase. The one or more gait characteristics may include a propulsion duration, a propulsion acceleration, a mid-stance speed, a speed norm, a toe-off speed, and a mid-swing speed. In some embodiments, the one or more gait characteristics may include a propulsion efficiency calculated based on other gait characteristics, such as gait characteristics related to a propulsion phase.

A risk level of the lower extremity may be determined based, at least in part, on the gait characteristics. For example, a processing station may analyze gait characteristics for features similar to those present in patients at a high risk of one or more medical problems. For example, one or more gait characteristics may be analyzed to determine whether the gait characteristics are outside a predetermined healthy range. Determination of a risk level of a lower extremity may include determination of a frailty of the lower extremity based, at least in part, on the gait characteristics. Lower extremities with high frailty may be more susceptible to medical conditions, such as fractures, ulcers, foot deformity, and other conditions. The frailty determination may include a determination of whether the lower extremity is non-frail, pre-frail, or frail. Alternatively or additionally, a frailty score on a scale of 0 to 100 may be provided to allow for increased granularity in frailty analysis. In some embodiments, a neural network model may be applied to a collection of stored motion data from users to select gait characteristics for use in determining the risk level of the lower extremity. For example, a neural network model may be applied to the data to determine which gait characteristics are correlated with higher risk, and such gait characteristics may be analyzed in determining the risk level of the lower extremity. In some embodiments, other types of data mining such as machine learning, deep learning, and generalized linear modelling may be applied to determine risk factors.

The analysis and processing described above may be performed by the processing station to analyze the motion data to determine a risk level of the lower extremity. Information processed by the processing station may be collected by a sensing device regarding motion of a lower extremity. A sensing device may include a sensor, such as a gyroscope or accelerometer, configured to sense motion of a lower extremity of the user. The sensing device may also include a wireless transmitter coupled to the sensor configured to wirelessly transmit motion data regarding motion of the lower extremity of the user to a processing station through a network for risk level analysis. The sensing device may be a wearable, an implant, or other sensing device. A processing station may receive the motion data from the sensing device and may calculate one or more gait characteristics based, at least in part, on the received motion data. The processing station may use the calculated gait characteristics to determine a risk level of the lower extremity of the user. In some embodiments, some or all of the analysis may be performed by a processing station integrated with the sensing device, such as when components are coupled to the sensors within a shared housing or such as when the sensor and processing circuitry are contained on the same integrated circuit.

The steps described herein may be included in code of a computer program product for execution by a computing device to carry out certain steps of the disclosure. For example, a processing station may execute a computer program to perform steps of receiving, calculating, and determining, as disclosed herein.

The foregoing has outlined rather broadly certain features and technical advantages of embodiments of the present invention in order that the detailed description that follows may be better understood. Additional features and advantages will be described hereinafter that form the subject of the claims of the invention. It should be appreciated by those having ordinary skill in the art that the conception and specific embodiment disclosed may be readily utilized as a basis for modifying or designing other structures for carrying out the same or similar purposes. It should also be realized by those having ordinary skill in the art that such equivalent constructions do not depart from the spirit and scope of the invention as set forth in the appended claims. Additional features will be better understood from the following description when considered in connection with the accompanying figures. It is to be expressly understood, however, that each of the figures is provided for the purpose of illustration and description only and is not intended to limit the present invention.

BRIEF DESCRIPTION OF THE DRAWINGS

For a more complete understanding of the disclosed system and methods, reference is now made to the following descriptions taken in conjunction with the accompanying drawings.

FIG. 7A is a graph of propulsion duration for non-frail, pre-frail, and frail users determined from collected user motion data according to some embodiments of the disclosure.

FIG. 7B is a graph of propulsion acceleration for non-frail, pre-frail, and frail users determined from collected user motion data according to some embodiments of the disclosure.

FIG. 7C is a graph of mid-stance speed for non-frail, pre-frail, and frail users determined from collected user motion data according to some embodiments of the disclosure.

FIG. 8A is a graph of speed norm for non-frail, pre-frail, and frail users determined from collected user motion data according to some embodiments of the disclosure.

FIG. 8B is a graph of toe-off speed for non-frail, pre-frail, and frail users determined from collected user motion data according to some embodiments of the disclosure.

FIG. 8C is a graph of mid-swing speed for non-frail, pre-frail, and frail users determined from collected user motion data according to some embodiments of the disclosure.

DETAILED DESCRIPTION

Motion data for a lower extremity may be received and analyzed to determine if the lower extremity is at risk of a variety of maladies. For example, motion data, such as angular velocity and/or foot acceleration collected while an individual is walking or running, received from a sensor may be used to calculate one or more gait characteristics. Gait characteristics may include a propulsion duration, a propulsion acceleration, a propulsion velocity, a mid-swing speed, a mid-stance speed, a foot speed during propulsion in planes perpendicular to a direction of walking, and a variation of gait characteristics while walking. Gait characteristics may further include a propulsion efficiency, calculated using gait characteristics from a propulsion phase. When a continuous walking bout was detected, gait characteristics may further include exhaustion, calculated by reduction in propulsion efficiency over walking steps. The gait characteristics may be used to determine a risk level of the lower extremity. For example, gait characteristics may indicate whether the lower extremity is at risk of a number of conditions, such as frailty, foot pain, foot deformity, foot ulcers, windlass failure, lower extremities injury, and risk of limb amputation. In some cases, a treatment, or an adjustment to an existing treatment, may be recommended to reduce a risk level and avoid conditions that may negatively impact the lower extremity.

Figure 1:
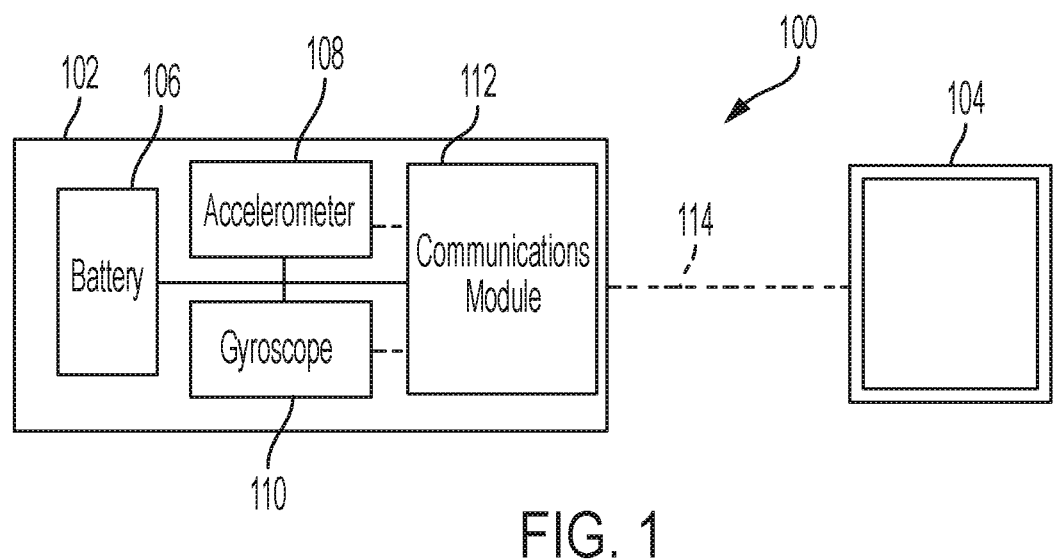
FIG. 1 is an illustration of a sensing device and a processing station for collection and analysis of motion data according to some embodiments of the disclosure.
Figure 2:
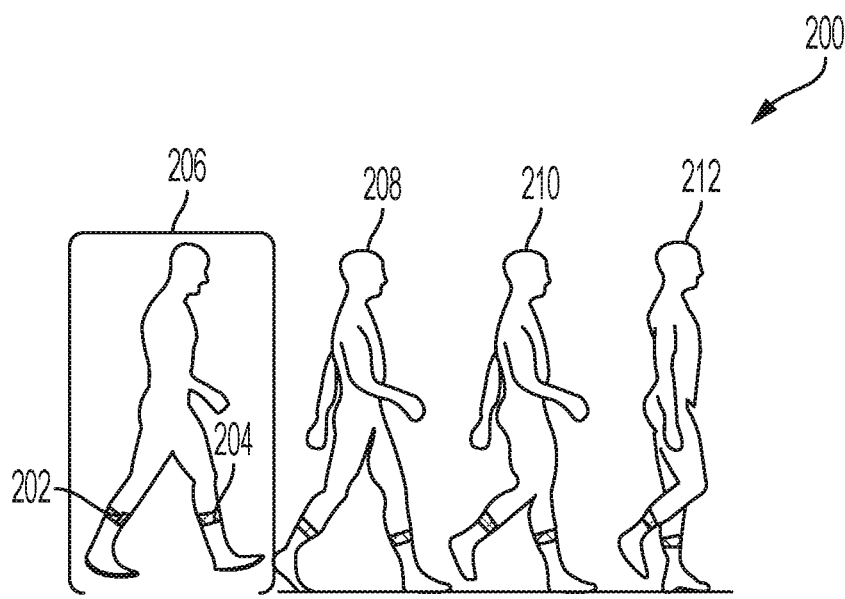
FIG. 2 is an illustration of a patient wearing sensing devices to collect motion data while moving through a gait cycle according to some embodiments of the disclosure.

Motion data collected by a sensing device attached to a lower extremity of a user may be transmitted to a processing station for analysis. An example system 100 for collection and analysis of lower extremity motion data is shown in FIG. 1. A sensing device 102 may include one or more sensors, such as inertial sensors, for detection motion of a lower extremity, such as a leg. For example, the sensing device 102 may be attached to a leg via adhesive, a strap, hooks and eyes, or other attachment mechanism. In some embodiments, a sensing device 102 may be woven into a sock or integrate in shoes, insoles, offloading, sandal, or other type of footwears. In some embodiments, a sensing device 102 may be an optical motion tracking system, such as a system including a webcam, digital camera, or other image or audio tracking device, configured to track motion of a user's leg. In other embodiments, the sensing device 102 may be integrated into an article of clothing or implanted in a lower extremity of a user. The sensing device 102 may include an accelerometer 108 for detecting acceleration of a lower extremity of a patient. The sensing device 102 may include a gyroscope 110 for collecting rotational and directional motion data. In some embodiments, the sensing device 102 may include a gyroscope 110, but not an accelerometer 108. The gyroscope 110 may provide advantages such as insensitivity to sensor location, allowing for integration into a wide array of wearables such as shoes, socks, pressure offloading footwear, and ankle braces. The sensing device 102 may include a battery 106 for powering the internal components of the sensing device 102. The sensing device 102 may include a communications module 112 for communicating with a processing station 104. The communications module 112 may, for example, be a wireless communications module for communicating with the processing station 104 via a wireless connection such as a Bluetooth, Wi-Fi, cellular, or other wireless connection. In some embodiments, the communications module 112 may include a physical port for physically connecting to the processing station 104. The sensing device 102 may include a memory (not shown) for storing motion data sensed by the sensors 108, 110. For example, a sensing device 112 may be worn by a user out of range of a wireless connection and may store motion data in a memory for transmission at a later time.

The sensing device 102 may connect to the processing station 104 via a connection 114. The connection 114 may be a connection over a wireless network, such as a Bluetooth connection or a connection over a local Wi-Fi network or cellular network, and/or a wired connection between the sensing device 102 and the processing station 104. For example, the sensing device 102 may communicate with the processing station 104 via a Bluetooth connection. In some embodiments the processing station 104 may be connected to the sensing device 102 to configure the sensing device 102. The processing station 104 may be a tablet, a laptop, a desktop, a server, a smart phone, or other computing platform capable of processing motion data. The processing station 104 may receive motion data from the sensing device 102 and may analyze the received motion data to determine lower extremity risk level. For example, the processing station 104 may process motion data to determine one or more gait characteristics for a lower extremity of a user and may determine whether the gait characteristics are indicative of a high lower extremity risk.

A user may wear one or more sensing devices as they go about their daily life to collect motion data from one or both lower extremities, allowing for continuous analysis of lower extremity performance outside of controlled observed environments. For example, sensing devices may be integrated in clothing and/or worn on or in a shin, foot, or leg of a user to sense motion data for transmission to a processing station for analysis. An example diagram of a walking user wearing two sensing devices is shown in FIG. 200. A user in a first phase 206 of a gait cycle may wear a first sensing device 204 on a right leg and a second sensing device 202 on a left leg. A sensing device 204 may also be worn on an ankle of a user or integrated into an article of clothing of a user, such as a sock or shoe. A single sensing device, however, may sometimes be sufficient for collection of motion data for determination of a risk level of a lower extremity and/or user. In some embodiments, a sensing device may be attached to a user's skin, or even implanted inside a lower extremity of a user. Tattoo sensors, injectable sensors, and impenetrable sensors may be used as sensing devices. As a user walks, the user may progress through a second phase 208 of a gait cycle, a third phase 210, of a gait cycle, and a fourth phase 212 of a gait cycle. The sensing devices 202, 204 may include gyroscopic sensors for collecting three-dimensional angular velocity data. In some embodiments, sensing devices 202, 204 may collect angular velocity data along a sagittal plane. The X-axis of sensing devices 202, 204 may, for example, be aligned along a tibia of a user, while a Z-component of movement, such as a mediolateral axis, of sensing devices 202, 204 may be used to determine angular velocity in the sagittal plane. A propulsion phase may occur near an end of a stance phase of a gait cycle. For example, the propulsion phase may begin before the first phase 206 when a user lifts their heel from the ground, and may end following the second phase 208, when a user lifts their toe from the ground. Motion data gathered during a propulsion phase may be particularly useful in analyzing gait characteristics indicative of a risk level of a lower extremity.

Figure 3:
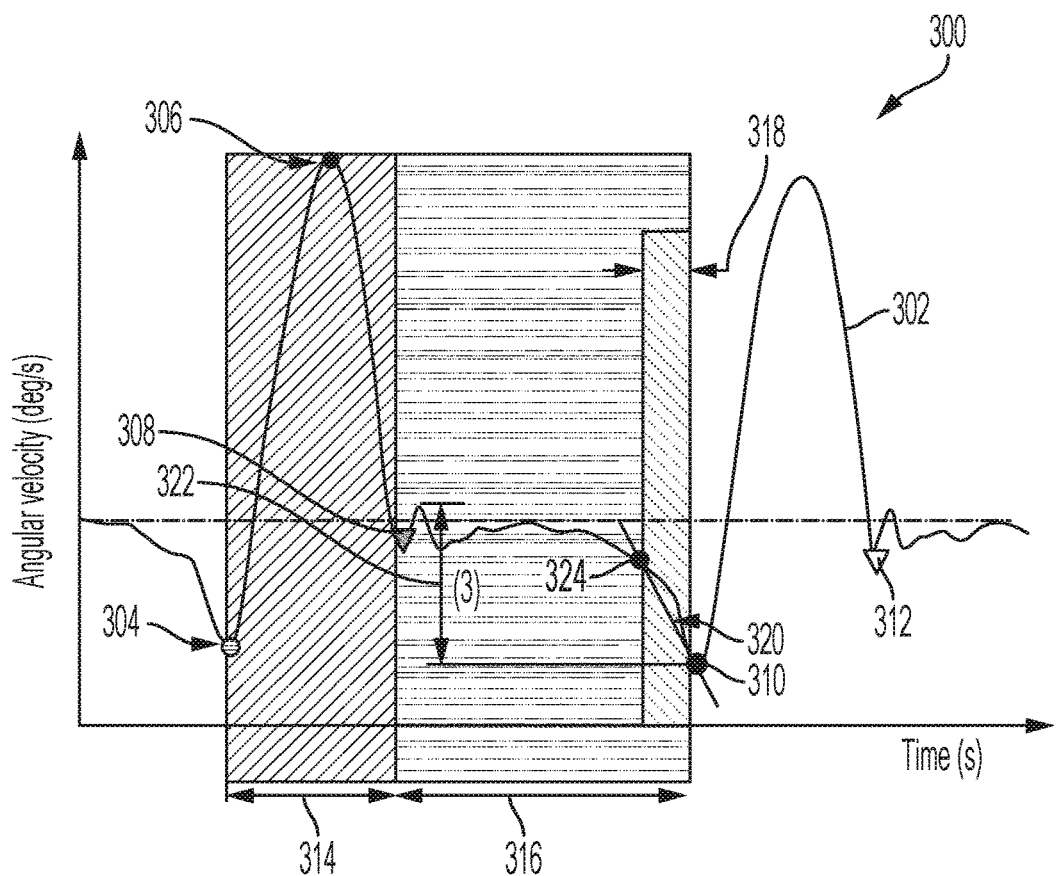
FIG. 3 is a graph of angular velocity data collected by a sensing device as a user moves through a gait cycle according to some embodiments of the disclosure.

Angular velocity data collected by a sensor may be used to determine a variety of gait characteristics. An example graph 300 of angular velocity 302 in a sagittal plane collected across a gait cycle is shown in FIG. 3. Angular velocity 302 data may, for example, be collected by a sensor attached to a lower extremity of a user while walking. Angular velocity data may be analyzed to detect a variety of events, which can be used to determine gait characteristics. A toe-off event may occur at point 304, where a minimum angular velocity is detected. Determined gait characteristics may, for example, include a toe-off speed, in degrees per second, such as a speed at point 304. The toe off event, at point 304, may initiate a swing phase 314. An angular velocity maximum, such as the maximum at point 306, may indicate a mid-swing point of a lower extremity of a user during the swing phase 314. Determined gait characteristics may, for example, include a mid-swing speed, in degrees per second, such as the mid-swing speed at point 306. Point 308 may indicate a heel strike, signifying the end of the swing phase 314 and the beginning of the stance phase 316. A propulsion phase 318 may occur near the end of the stance phase 316. The propulsion phase 318 may, for example, begin at a heel off at point 324 and end at a toe off, at point 310. The propulsion phase 318 and the stance phase 316 may end at the toe off, at point 310. A propulsion acceleration 320 may be determined by calculating a slope of the angular velocity between a heel off, at point 324, and a toe off, at point 310. Determined gait characteristics may, for example, include a propulsion acceleration 320 in degrees per second squared. A mid-stance speed 322 may be determined by calculating the difference between a maximum angular velocity of the stance phase and a minimum angular velocity of the stance phase. Determined gait characteristics may also include a mid-stance speed 322 in degrees per second. Additionally, determined gait characteristics may include a duration of the propulsion phase 318 and a speed norm in degrees per second, which may be calculated may determining a magnitude of a vector sum of the angular velocity in the transverse and frontal plane. Gait characteristics may also include a propulsion efficiency, determined through analysis of propulsion phase 318 gait characteristics. Gait characteristics may also include exhaustion determined by decline in propulsion efficiency over time. Thus, a variety of gait characteristics, such as toe-off speed, mid-swing speed, mid-stance speed, propulsion duration, propulsion acceleration, and speed norm, may be determined based on sensed angular velocity.

Figure 4:
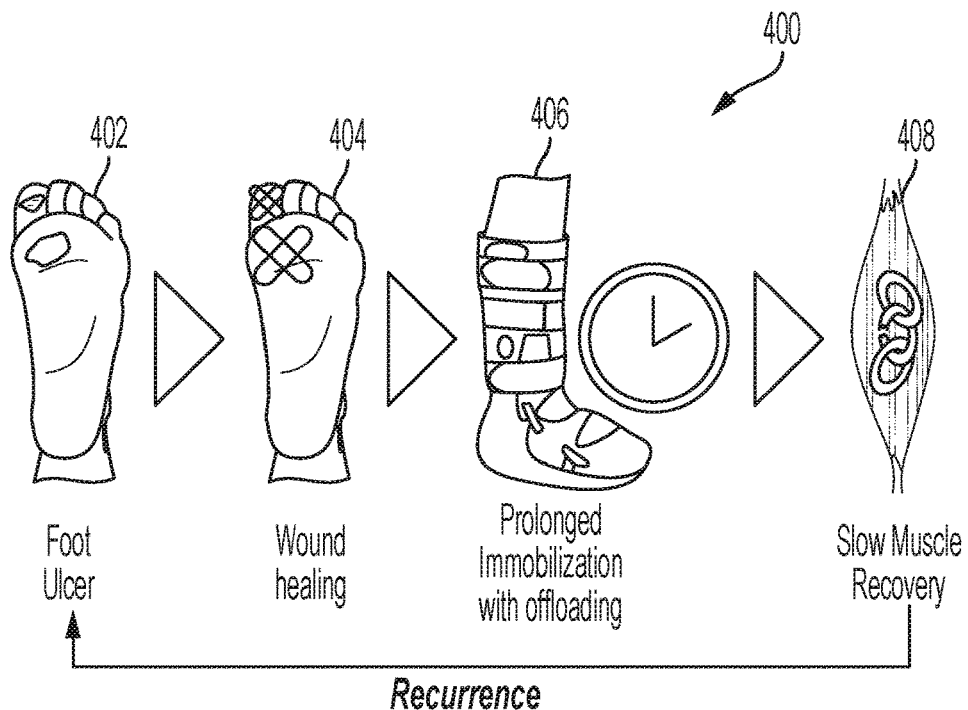
FIG. 4 is an illustration of a progression of a foot recovery and recurrence process.

Gait characteristics may be used to determine a risk of a lower extremity. Treatment plans for lower extremities can, in some cases, have a negative impact on lower extremity performance and may increase a lower extremity risk level. For example, a progression 400 of foot recovery from a foot ulcer is shown in FIG. 4. At step 402 a foot ulcer may be discovered on a foot of an individual. At step 404, the foot ulcer may begin to heal. At step 406, a prolonged immobilization of the foot may be instituted in an attempt to aid recovery from the foot ulcer or another condition. At step 408, slow muscle recover may occur due to the prolonged immobilization, which may increase a risk of redevelopment of foot ulcers. For example, muscle atrophy and frailty may result from the prolonged immobilization, increasing a risk of foot ulcers. The slow muscle recovery at step 408 may lead to a recurrence of the foot ulcer. Analysis of gait characteristics can help to predict effectiveness of treatment options, such as prolonged immobilization, and can determine a risk level of a lower extremity as treatment progresses. For example, a risk of recurrence of foot ulcers or slow recovery in gait performance following a period of prolonged immobilization may be determined based on gait characteristics. Such a determination may be used to adjust a treatment plan, to minimize a risk of ulcer recurrence and/or muscle atrophy.

Figure 5:
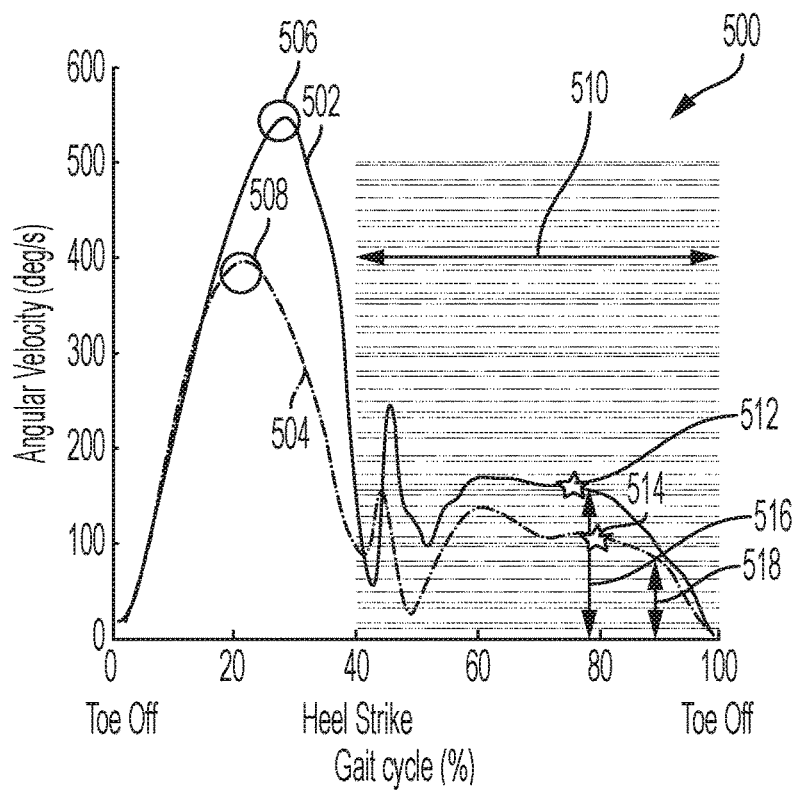
FIG. 5 is a graph of angular velocity of a user's leg measured by a sensing device during a gait cycle according to some embodiments of the disclosure.
Figure 6:
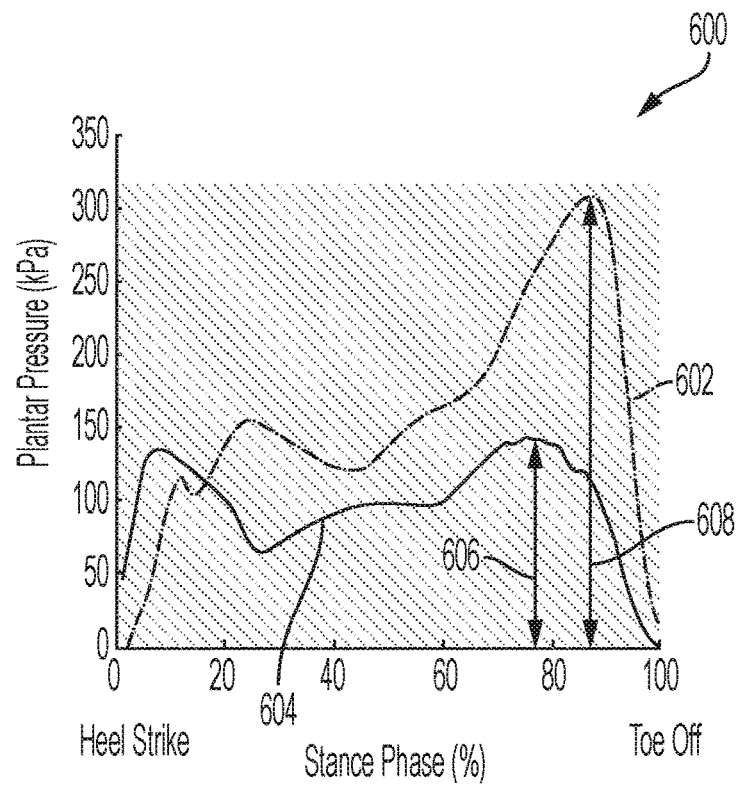
FIG. 6 is a graph of plantar pressure of a user's foot measured by sensing device during a stance phase of a gait cycle according to some embodiments of the disclosure.

Gait characteristics may differ between healthy individuals and individuals with a high lower extremity risk level. An example angular velocity 502 of a lower extremity of a healthy individual compared with an example angular velocity 504 of an individual with high lower extremity risk is shown in FIG. 5. A mid-swing velocity 506 of a healthy individual may be greater than a mid-swing velocity 508 of an individual with a high lower extremity risk. Analysis of a stance phase 510, and a propulsion phase in particular, may be particularly useful for distinguishing between healthy individuals and individuals with high lower extremity risk. The stance phase may, for example, begin with a heel strike and end with a toe-off of the individual. A propulsion speed 516 of a healthy individual may be greater than a propulsion speed 518 of an individual with a high lower extremity risk level. Furthermore, a mid-stance velocity 512 for a healthy individual may be greater than a mid-stance velocity 514 of an individual with a high lower extremity risk level. Propulsion efficiency characteristics, such as angular velocity, propulsion speed, mid-swing velocity, mid-stance velocity, and other characteristics may be used to determine a foot pressure during the stance phase 510. Foot pressure may contribute to foot risk. FIG. 6 is a graph 600 showing plantar pressure 604 of a healthy individual compared to plantar pressure 602 of an individual with a high lower extremity risk level during a stance phase of a gait cycle. Plantar pressures 604, 602 may be derived from propulsion efficiency characteristics determined based on angular velocity, as described with respect to FIG. 5. As shown in FIG. 6, a peak pressure 606 during a propulsion phase, for a healthy individual, is less than a peak pressure 608 for an individual with a high lower extremity risk level during a propulsion phase. High peak pressure can be indicative of a high lower extremity risk level. For example, high peak pressure can increase the risk of foot deformity, such as bunions, hammer toes, overlapping toes, and other deformities, a risk of plantar ulcers, and even a risk of lower extremity amputation. Thus, gait characteristics, such as propulsion efficiency characteristics and plantar pressure characteristics may be indicative of and may be used to determine a risk level of an individual.

Determination of a risk level of an individual may include determining a frailty of the individual as frailty may indicate a heightened risk for various lower extremity maladies. Gait characteristics of the individual, particularly during the propulsion phase, may indicate whether an individual is non-frail, pre-frail, or frail. FIGS. 7A-C and 8A-C are graphs of average gait characteristics for groups of non-frail, pre-frail, and frail individuals. Adults with an age greater than or equal to fifty-five were gathered and assessed for frailty using the Fried frailty phenotype assessment, analyzing phenotypes such as unintentional weight loss, weakness, self-reported exhaustion, slowness, and physical activity. Based on the frailty phenotype assessment, individuals were classified as non-frail, pre-frail, and frail. For example, individuals that exhibited zero phenotypes were classified as non-frail, individuals that exhibited one to two phenotypes were classified as pre-frail, and individuals that exhibited three or more phenotypes were classified as frail. The values shown in FIGS. 7A-C and 8A-C were calculated from right leg acceleration data of a group of 161 individuals, with 49 classified as non-frail, 92 classified as pre-frail, and 20 classified as frail. The individuals were then asked to perform a trial of a 4.57 meter free and unobstructed walking task at a self-selected pace while three-dimensional angular velocity data was collected using gyroscopic sensing devices attached to lower extremities. The angular velocity data was used to calculate a variety of gait characteristics, such as speed norm, toe-off speed, mid-swing speed, propulsion duration, propulsion acceleration, and mid-stance speed. As shown by graphs in FIGS. 7A-C and 8A-C, gait characteristics differed substantially among frail, pre-frail, and non-frail individuals FIG. 7A is a graph 700 of average propulsion duration, an example gait characteristic, calculated based on sensed right leg angular velocity data for a group of individuals. A propulsion duration may, for example, be a time difference between a heel-off and a toe-off. The average propulsion duration 702 for non-frail individuals was approximately 0.7 seconds. The average propulsion duration 704 for pre-frail individuals was. 83 seconds. The average propulsion duration for frail individuals was 1.12 seconds. As shown in FIG. 7A, non-frail propulsion duration 702 was seventeen percent less than pre-frail propulsion duration 704, with a Cohen's d of 0.48, and fifty-eight percent less than frail propulsion duration 706, with a Cohen's d of 1.65. Pre-frail propulsion duration 704 was thirty-five percent less than frail propulsion duration 704, with a Cohen's d of 1.17. Thus, propulsion duration, as calculated based on right leg angular velocity data, differs substantially from frail, to pre-frail, to non-frail individuals. Propulsion duration is also highly correlated with frailty phenotypes. For example, using Spearman's correlation (rho), propulsion duration is positively correlated with weakness, with a rho of 0.36, slowness, with a rho of 0.684, and exhaustion, with a rho of 0.234. Each of these described values, and others described below, can be determined by the processing station during analysis of the collected motion data.

FIG. 7B is a graph 710 of average propulsion acceleration, an example gait characteristic, calculated based on sensed right leg angular velocity data for a group of individuals. The average propulsion acceleration may, for example, be a change in angular velocity during the propulsion phase. The average non-frail propulsion acceleration 712, in degrees per second squared, was approximately 362. The average pre-frail propulsion acceleration 714 was approximately 308. The average frail propulsion acceleration 716 was approximately 197. Non-frail propulsion acceleration 712 was fifteen percent greater than pre-frail propulsion acceleration 714, with a Cohen's d of 0.43, and forty-five percent greater than frail propulsion acceleration 716, with a Cohen's d of 1.28. Pre-frail propulsion acceleration 714 was thirty-five percent greater than frail propulsion acceleration 716, with a Cohen's d of 0.86. Thus, propulsion acceleration, as calculated based on right leg angular velocity data, differs substantially from frail, to pre-frail, to non-frail individuals. Propulsion acceleration is also negatively correlated with frailty phenotypes. For example, propulsion acceleration is negatively correlated with weakness, with a rho of −0.257, and slowness, with a rho of −0.687.

FIG. 7C is a graph 720 of average mid-stance speed, an example gait characteristic, calculated based on sensed right leg angular velocity data for a group of individuals. A mid-stance speed may, for example, be a magnitude of the largest difference in angular velocity during a stance phase, between heel-strike and toe-off. The average non-frail mid-stance speed 722, in degrees per second, was approximately 137. The average pre-frail mid-stance speed 724 was approximately 122. The average frail mid-stance speed 726 was approximately 98. Non-frail mid-stance speed 722 was eleven percent greater than pre-frail mid-stance speed 724, with a Cohen's d of 0.41, and twenty-eight percent greater than frail mid-stance speed 726, with a Cohen's d of 1.07. Pre-frail mid-stance speed 724 was twenty percent greater than frail mid-stance speed 726, with a Cohen's d of 0.66. Thus, mid-stance speed, as calculated based on right leg angular velocity data, differs substantially from frail, to pre-frail, to non-frail individuals. Mid-stance speed is also negatively correlated with frailty phenotypes. For example, mid-stance speed is negatively correlated with slowness, with a rho of −0.553.

FIG. 8A is a graph 800 of average speed norm, an example gait characteristic, calculated based on sensed right leg angular velocity data for a group of individuals. A speed norm may, for example, be a magnitude of a vector sum of angular velocity in the frontal and transverse plane. The average non-frail speed norm 802, in degrees per second, was approximately 191. The average pre-frail speed norm 804 was approximately 173. The average frail speed norm 806 was approximately 130. Non-frail speed norm 802 was eleven percent greater than pre-frail speed norm 804, with a Cohen's d of 0.33, and thirty-two percent greater than frail speed norm 806, with a Cohen's d of 1.08. Pre-frail speed norm 804 was twenty-five percent greater than frail speed norm 806, with a Cohen's d of 0.75. Thus, speed norm, as calculated based on right leg angular velocity data, differs substantially from frail, to pre-frail, to non-frail individuals. Speed norm is also negatively correlated with frailty phenotypes. For example, speed norm is negatively correlated to weakness, with a rho of −0.330, slowness, with a rho of −0.543, exhaustion, with a rho of −0.248, and physical activity, with a rho of −0.212. Thus, speed norm is negatively correlated with all analyzed frailty phenotypes apart from weight loss.

FIG. 8B is a graph 810 of average toe-off speed, an example gait characteristic, calculated based on sensed right leg angular velocity data for a group of individuals. A toe-off speed may, for example be a magnitude of angular velocity at toe-off. The average non-frail toe-off speed 812, in degrees per second, was approximately 147. The average pre-frail toe-off speed 814 was approximately 120. The average frail toe-off speed 816 was approximately 83. Non-frail toe-off speed 812 was eighteen percent greater than pre-frail toe-off speed 814, with a Cohen's d of 0.52, and forty-three percent greater than frail toe-off speed 816, with a Cohen's d of 1.24. Pre-frail toe-off speed 814 was thirty-one percent greater than frail toe-off speed 816, with a Cohen's d of 0.72. Thus, toe-off speed, as calculated based on right leg angular velocity data, differs substantially from frail, to pre-frail, to non-frail individuals. Toe-off speed is also negatively correlated with frailty phenotypes. For example, toe-off speed is negatively correlated to weakness, with a rho of −0.402, slowness, with a rho of −0.646, and exhaustion, with a rho of −0.205.

FIG. 8C shows a graph 820 of average mid-swing speed, an example gait characteristic, calculated based on sensed right leg angular velocity data for a group of individuals. A mid-swing speed, may, for example, be a magnitude of an angular velocity at mid-swing. The average non-frail mid-swing speed 822, in degrees per second, was approximately 338. The average pre-frail mid-swing speed 824 was approximately 287. The average frail mid-swing speed 826 was approximately 197. Non-frail mid-swing speed 822 was fifteen percent greater than pre-frail mid-swing 824, with a Cohen's d of 0.73, and thirty-one percent greater than frail mid-swing speed 826, with a Cohen's d of 1.55. Pre-frail mid-swing speed 824 was twenty percent greater than frail mid-swing speed 826, with a Cohen's d of 0.82. Thus, mid-swing speed, as calculated based on right leg angular velocity data, differs substantially from frail, to pre-frail, to non-frail individuals. Mid-swing speed is also negatively correlated with frailty phenotypes. For example, toe-off speed is negatively correlated to weakness, with a rho of −0.358 and slowness, with a rho of −0.784. Similar differences between non-frail, pre-frail, and frail individuals are present in angular velocity data collected for left leg movement, showing that motion data from either a left leg sensor or a right leg sensor may be used to determine frailty.

Figure 9:
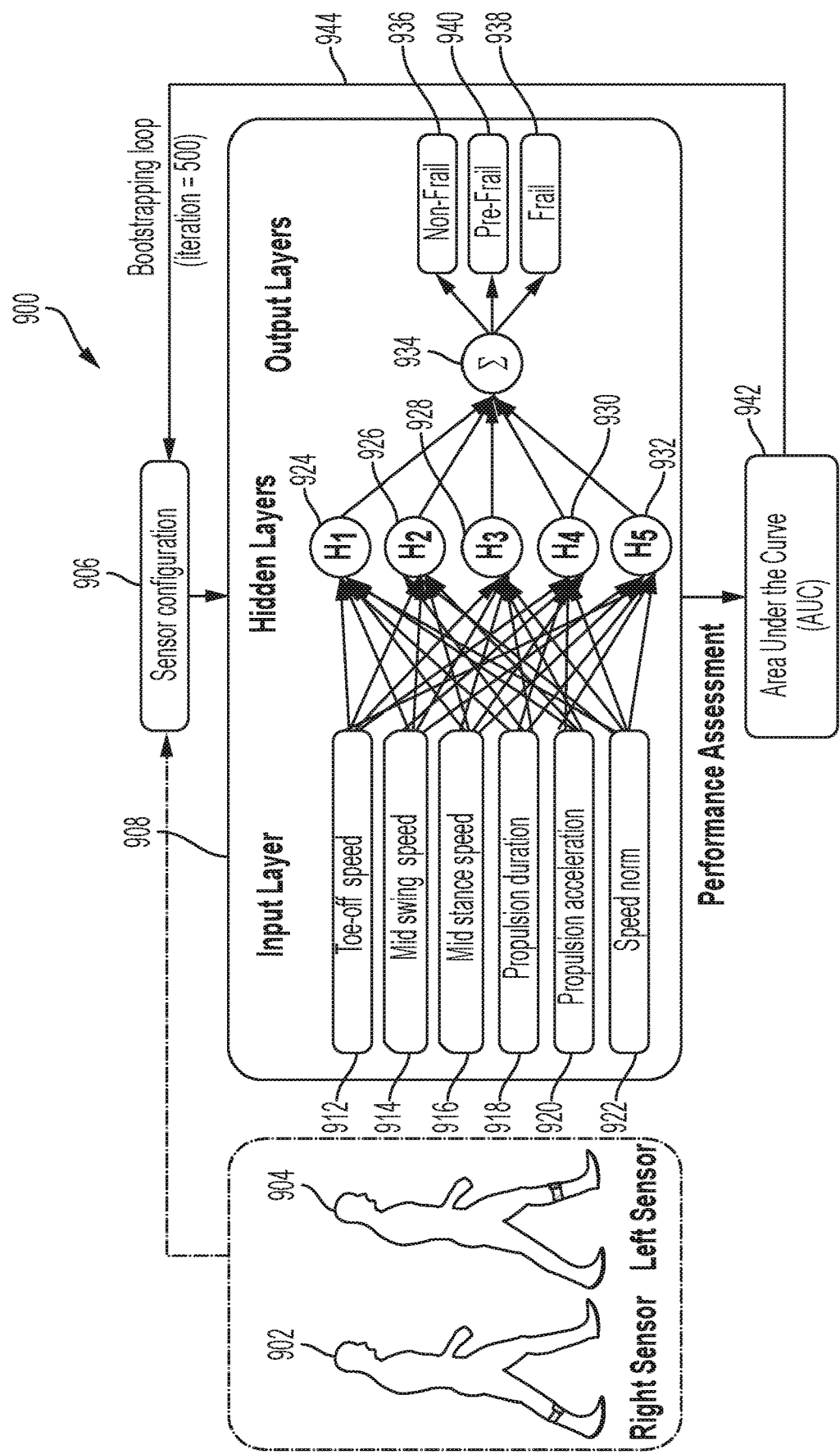
FIG. 9 is a block diagram of an example neural network model for analyzing the predictive aspects of gait characteristics according to some embodiments of the disclosure.

A neural network model 900, as shown in FIG. 9, may be used to analyze lower extremity motion data and establish reliability of a predictive relationship between gait characteristics and a frailty level. For example, a neural network model may determine whether it is possible to accurately predict a frailty level based on a set of gait characteristics. The neural network 900 may analyze a discriminating power of gait characteristics 912-922 to differentiate between non-frail, pre-frail, and frail individuals. The neural network model may receive input data from a right leg sensor 902 and/or a left leg sensor 904, such as angular velocity data from gyroscopes of the left and right leg sensors 902, 904 at a sensor configuration 906. Sensed data, such as angular velocity data, may be input into a neural network processing algorithm 908. For example, various gait characteristics, such as toe-off speed 912, mid-swing speed 914, mid-stance speed 916, propulsion duration 918, propulsion acceleration 920, and speed norm 922, may be determined using sensed data and fed into the neural network processing algorithm at an input layer. The neural network processing algorithm 908 may, for example, be an 8-fold neural network algorithm with five layers of hidden nodes, using eight subsets of motion data for processing. Gait characteristics for a training data set and validation data set may be input into the neural network processing algorithm 908. The neural network processing algorithm 908 may be repeated multiple times using multiple sets of validation data. A plurality of hidden layers 924-932 may process the received gait characteristics 912-922 to determine correlations between the gait characteristics and a frailty level. The outputs of the hidden layers may be summed at sum block 934 and used to determine whether the characteristics indicate an individual that is non-frail 936, pre-frail 940, or frail 938. The results of the neural network processing algorithm 908 may be output for performance assessment, and an area under curve 942 may be calculated. The area under curve 942 may, for example, indicate an accuracy of a determination, based on gait characteristics, whether gait characteristics of the input data belonged to an individual classified as frail, pre-frail, or non-frail. The area under curve may be fed back 944 to a sensor configuration 906, and used to adjust the algorithm in a bootstrapping loop, which may include greater or less than 500 iterations with random resampling of data to generate multiple different validation and training sets. For example, the neural network algorithm may be repeated until a ninety-five percent confidence interval is achieved to establish reliability of the predictive relationship between gait characteristics and frailty levels.

Figure 10C:
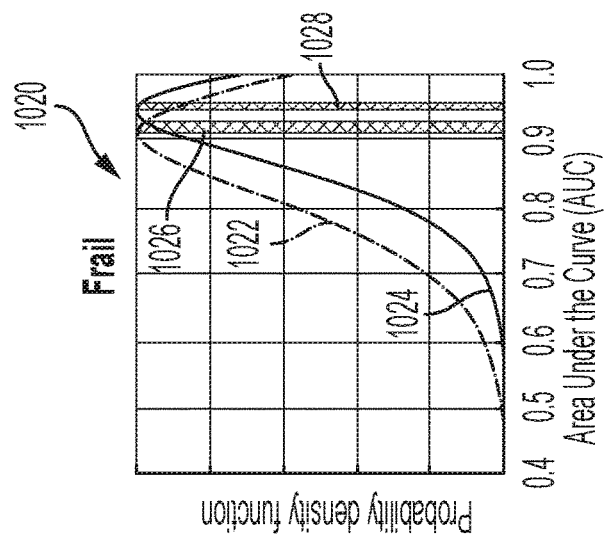
FIG. 10C is a graph of an accuracy of a neural network model for analysis of gait characteristics of frail users determined from collected user motion data according to some embodiments of the disclosure.
Figure 10B:
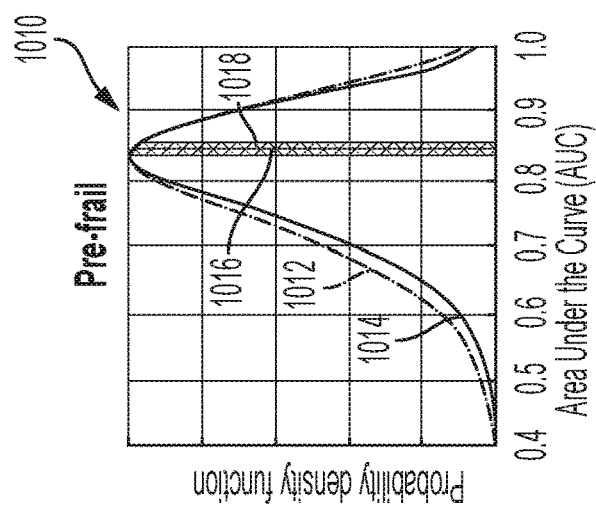
FIG. 10B is a graph of an accuracy of a neural network model for analysis of gait characteristics of pre-frail users determined from collected user motion data according to some embodiments of the disclosure.
Figure 10A:
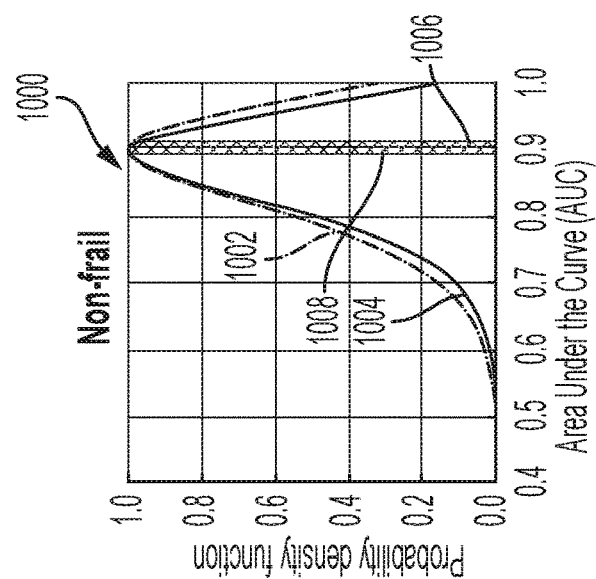
FIG. 10A is a graph of an accuracy of a neural network model for analysis of gait characteristics of non-frail users determined from collected user motion data according to some embodiments of the disclosure.

Use of a neural network model can establish a predictive relationship between gait characteristics and a frailty level with a high degree of accuracy. FIGS. 10A-C show a probability density function as a function of area under curve demonstrating an accuracy of neural network models using bootstrapping. For example, using only data from a sensor on a left leg, a lower and upper bound of area under curve determined using the algorithm described with respect to FIG. 9 is approximately 0.900 to 0.913 for non-frail individuals, 0.838 to 0.854 for pre-frail individuals, and 0.945 to 0.958 for frail individuals. A probability density function for left leg data 1002 and a probability density function for right leg data 1004 is shown in FIG. 10A. FIG. 10A shows a high right leg confidence interval 1008 and a high left leg confidence interval 1006. A probability density function for left leg data 1012 and a probability density function for right leg data 1014 is shown in FIG. 10B. FIG. 10B shows a high right leg confidence interval 1018 and a high left leg confidence interval 1016. A probability density function for left leg data 1022 and a probability density function for right leg data 1024 is shown in FIG. 10C. FIG. 10C shows a high right leg confidence interval 1028 and a high left leg confidence interval 1026. Thus, the lowest area under curve for classification of frailty was for data from pre-frail individuals.

Figure 11:
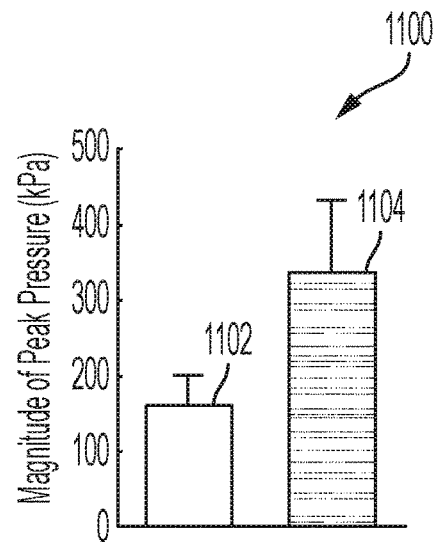
FIG. 11 is a graph of a peak pressure for frail and non-frail users determined from collected user motion data according to some embodiments of the disclosure.

Frailty status can be indicative of a variety of lower extremity maladies. For example, frailty status is highly correlated with increased peak plantar pressure which may be predictive of a variety of foot risks, such as a risk of development of foot ulcers and/or foot deformity. FIG. 11 shows an example bar graph 1100 comparing an average peak plantar pressure of a group of non-frail individuals and a group of frail individuals. As shown in FIG. 11, an average peak plantar pressure 1102 of non-frail individuals is approximately 150 kPa, while an average peak plantar pressure 1104 of frail individuals is approximately 320 kPa. Thus, average plantar pressure for frail individuals is approximately 109% greater than average plantar pressure for non-frail individuals. The increased plantar pressure experienced by frail individuals may contribute to development of foot ulcers, foot deformity, and other lower extremity maladies. Thus, a frailty level of an individual can be a useful indicator of a lower extremity risk level of the individual.

Figure 12:
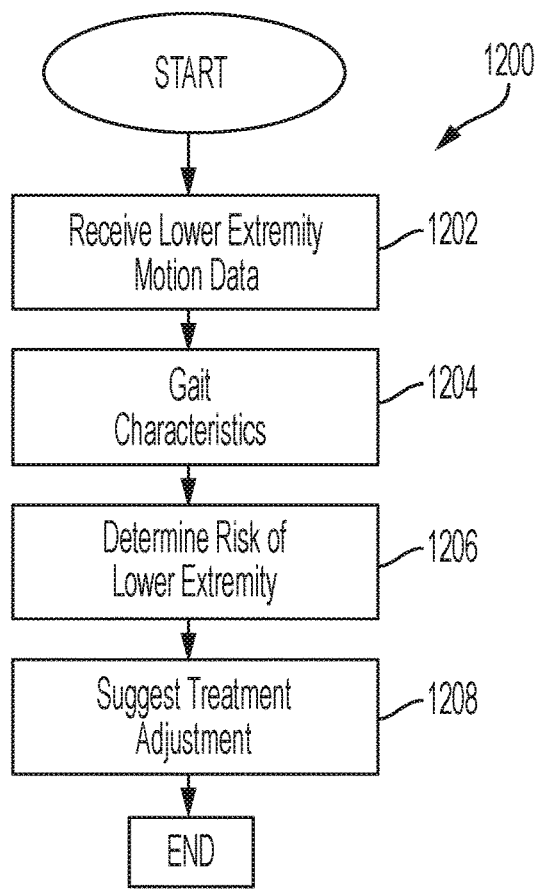
FIG. 12 is an example method for determining a risk of a lower extremity based on received motion data according to some embodiments of the disclosure.

Lower extremity motion data may be used to determine gait characteristics, which may be indicative of a risk level of a lower extremity of an individual. A method 1200 for analysis of lower extremity data is shown in FIG. 12. The method 1200 may begin at step 1202 with receipt of lower extremity motion data. For example, a processing station, such as a personal computer, laptop, tablet, server, or other processing station may receive lower extremity motion data, such as three-dimensional angular velocity data, from a sensor attached to a lower extremity of a user. The angular velocity data may, for example, be angular velocity data in a sagittal plane of a user collected while the user is walking. In some embodiments, motion data may be received from multiple sensing devices coupled left and right legs of a user. Sensing devices may be integrated in articles of clothing such as an ankle foot orthosis, an insole, an offloading, a sock, a shoe, an ankle brace, and other articles of clothing. Sensing devices may also be attached directly to a skin of a user, such as with an adhesive, strap, or other attachment mechanism. In some embodiments, sensing devices may be implanted in a leg, ankle, or foot of a user. A sensing device may be an optical sensor that observes movement of a lower extremity of a user, such as a cell phone, digital camera, or webcam. Sensing devices may include a gyroscope for collection and transmission of gyroscopic motion data, such as angular velocity. Lower extremity motion data may be received wirelessly. For example, a sensing device attached to a leg of a user may transmit motion data across a Bluetooth, Wi-Fi, or cellular connection as a user goes about daily activities. Such transmission may allow for collection of data outside of a controlled observed environment. In some embodiments, lower extremity motion data from multiple users may be aggregated at one or more servers in a data center.

At step 1204 gait characteristics may be calculated based, at least in part, on received lower extremity motion data. For example, when a processing device receives lower extremity motion data, such as angular velocity, it may use the lower extremity motion data to calculate a plurality of gait characteristics such as a toe-off speed, a mid-swing speed, a mid-stance speed, a propulsion duration, a propulsion acceleration, and a speed norm. Other gait characteristics may include a ratio of propulsion duration to stance duration, a ratio of propulsion acceleration to a mid-swing speed, and a ratio of an angular velocity norm in planes perpendicular to a direction of walking, such as transversal and frontal planes, to a propulsion acceleration. Foot movement may also be used as a gait parameter, such as by calculating a product of an angular velocity and an angular acceleration during a propulsion phase. A peak detection algorithm may be applied to angular velocity in the sagittal plane to identify the three phases of the gait cycle: the swing phase, the stance phase, and the propulsion phase. Gait characteristics may be calculated for multiple gait cycles as a user goes about daily activity and may be monitored for changes in gait characteristics over time, such as deviation of one or more gait characteristics from a set threshold range. In some embodiments an artificial neural network may be used to analyze gait characteristics to determine whether certain gait characteristics are able to predict frailty with high reliability. Gait characteristics from a propulsion phase of a gait cycle may be particularly useful. In some embodiments, calculation of gait characteristics may include identification and quantification of a propulsion phase based on the received lower extremity motion data. For example, identification of a propulsion phase may include identifying of a starting point, such as a heel-off event, and a stopping point, such as a toe-off event, of the propulsion phase. In some embodiments, a beginning of a propulsion phase may be identified based on a determination that an angular velocity of the lower extremity has exceeded a predetermined angular velocity, following a mid-stance position and preceding a toe-off condition. Quantification of the propulsion phase may include determination of a duration of the propulsion phase and/or an average acceleration during a propulsion phase. In some embodiments, quantification of the propulsion phase may also include calculating a norm of an angular velocity of the lower extremity in one or more planes perpendicular to a direction in which an individual is walking. One or more gait characteristics may be used to determine a propulsion efficiency. A propulsion efficiency may be a particularly useful gait characteristic, used to determine plantar pressure. Gait characteristics may also include values related to foot pressure, determined based on the motion data, such as a maximum plantar or forefoot pressure placed on the foot during a propulsion phase. Other useful gait characteristics may include a ratio of a propulsion efficiency to a maximum forefoot pressure during a propulsion phase and a ratio of a propulsion efficiency to a pressure time integral during a propulsion phase At step 1206, a risk level of a lower extremity may be determined. For example, a processing device determine a risk level of a lower extremity of a user of a sensing device using calculated gait characteristics. In some embodiments, a risk level of a lower extremity may be determined based, at least in part, on a propulsion efficiency. For example, a risk level may be determined based, at least in part, on a ratio of a propulsion efficiency to a maximum forefoot pressure during a propulsion phase or based, at least in part, on a ratio of a propulsion efficiency to a pressure time integral during a propulsion phase. Determination of a risk level of a lower extremity may include a determination of whether a foot is at risk of various maladies. For example, the risk level may be a risk level that an individual will experience one or more lower extremity maladies, such as a risk level that the individual will encounter foot pain, a fall, frailty, foot ulcers, and/or lower extremity amputation. The risk level may, for example, include a score of the lower extremity, such as a score of a foot, indicating a degree of risk that the lower extremity will encounter a negative condition. Gait characteristics may be highly correlated with a variety of lower extremity maladies, as discussed herein. A processing device may, for example, determine that a user has a high-risk level if a gait characteristic, such as a toe-off speed of a user, is outside a predetermined range. For example, if a propulsion efficiency calculated based on one or more gait parameters falls below a predetermined threshold, a determination may be made that a foot is at risk of diabetic foot ulcers or deformity, such as bunions, hammer toes, overlapping toes, and other deformities. The predetermined threshold may, for example, be determined by analyzing a library of gait characteristics collected for users at varying risk levels and determining a toe-off speed or propulsion efficiency below which a user is likely to be high risk. Determining a risk level of a lower extremity may, for example, include determining a frailty level, such as frail, non-frail, or pre-frail, of an individual. A frail individual may be at high risk of lower extremity maladies, particularly those resulting from increased plantar pressure, such as foot ulcers and/or lower extremity amputation. A determination of a risk and/or frailty level may be made using a linear or non-linear combination of gait characteristics.

Frailty analysis using gait characteristics may also provide more gradation than a simple frail, pre-rail, or non-frail rating. For example, a frailty score may be assigned to a lower extremity and/or an individual based on gait characteristics. Such gradation may allow for enhanced intervention providing physicians with additional detail to use in determining treatments.

At step 1208, a new treatment or an adjustment to an existing treatment may be suggested, to lower the determined risk level. For example, if an individual is determined to be frail a treatment regimen may be suggested to strengthen the individual and move the individual from a frail condition to a pre-frail or non-frail condition. Gait characteristics may be continuously calculated using motion data to determine changes in a risk and or frailty level over time. For example, if an increase in risk or frailty level is determined, a physical therapy regimen, custom orthotic insoles, insole modification, or other treatment method may be recommended for reducing risk and/or remedying the frail condition. When the condition is remedied, an alert may be provided to a patient or a doctor notifying the patient or doctor that resumption of standard treatment options, such as use of standard diabetic shoes, may be appropriate.

Analysis of gait characteristics can also allow for more reliable treatment plans to be implemented. For example, gait characteristics may be analyzed to determine if a treatment plan is likely to have a positive impact on a lower extremity risk level. A determination may also be made, based on gait characteristics, that one or more treatment options, such as offloading, lower extremity amputation, and/or foot surgery, may have a negative impact on a foot risk level and/or a frailty of an individual, and alternative treatment options with a greater likelihood of success may be suggested.

Monitoring of gait characteristics over time may be particularly useful in assessing the effectiveness of prescribed treatment regimens, such as specialized footwear, orthotics, lower extremity surgery, exercise, and physical therapy, for lower extremity maladies. For example, if a physical therapy regimen or a prescribed offloading causes deterioration in gait characteristics, such as propulsion efficiency, such deterioration may be detected and an individual or doctor may be informed, to allow for a treatment adjustment. Determination of a risk level may also include determination of a magnitude of muscle atrophy and/or unhealthy foot biomechanics following a lower extremity treatment. For example, if a physical therapy regimen is having a negative impact on a individual's leg, changes in gait characteristics of the individual may indicate an increased risk level, such as an increase in frailty. Offloading, for example, may have a negative impact on gait characteristics and propulsion efficiency. When an increase in risk level is detected, treatment adjustments may be recommended to mitigate a potential negative impact of the treatment on the lower extremity and to reduce a risk level of the lower extremity. In some embodiments, an alert may be generated for a user or for a doctor when an increase in risk level or frailty level is detected. In particular, an alert may be generated for a doctor when unhealthy recovery following healing of a wound, surgery, or amputation is detected, for example by detecting an increase in risk or frailty. Thus, motion data collected for one or more lower extremities of an individual can be used to determine a risk level of the individual and to recommend treatments or adjustments to existing treatments to reduce the risk level of the individual.

The schematic flow chart diagram of FIG. 12 is generally set forth as a logical flow chart diagram. As such, the depicted order and labeled steps are indicative of aspects of the disclosed method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagram, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The operations described above as performed by a controller may be performed by any circuit configured to perform the described operations. Such a circuit may be an integrated circuit (IC) constructed on a semiconductor substrate and include logic circuitry, such as transistors configured as logic gates, and memory circuitry, such as transistors and capacitors configured as dynamic random access memory (DRAM), electronically programmable read-only memory (EPROM), or other memory devices. The logic circuitry may be configured through hard-wire connections or through programming by instructions contained in firmware. Further, the logic circuitry may be configured as a general purpose processor capable of executing instructions contained in software. If implemented in firmware and/or software, functions described above may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise random access memory (RAM), read-only memory (ROM), electrically-erasable programmable read-only memory (EEPROM), compact disc read-only memory (CD-ROM) or other optical disk storage, magnetic disk storage or other magnetic storage devices, or any other medium that can be used to store desired program code in the form of instructions or data structures and that can be accessed by a computer. Disk and disc includes compact discs (CD), laser discs, optical discs, digital versatile discs (DVD), floppy disks and Blu-ray discs. Generally, disks reproduce data magnetically, and discs reproduce data optically. Combinations of the above should also be included within the scope of computer-readable media.

In addition to storage on computer readable medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims.

Although the present disclosure and certain representative advantages have been described in detail, it should be understood that various changes, substitutions and alterations can be made herein without departing from the spirit and scope of the disclosure as defined by the appended claims. For example, although motor-cognitive impairment testing is described for the iTMT platform, the platform may also be used for motor-cognitive exercise training, assessing risk of falling, predicting outcomes post-intervention, screening outcomes, predicting adverse events such as delirium, studying the brain, and/or evaluating dual tasking on certain brain region activation. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:
1. A method, comprising:
  receiving, wirelessly over a network by a processor from one or more sensors of a first sensing device worn on a first lower extremity of a user and from one or more sensors of a second sensing device worn on a second lower extremity of the user, motion data regarding motion of the first lower extremity and the second lower extremity over a period of time, wherein:

the first sensing device is one of: (i) integrated into a first article of clothing worn on a first leg, ankle, or foot of the first lower extremity, (ii) attached directly to a skin of the first leg, ankle, or foot of the first lower extremity via adhesive or a strap, or (iii) implanted in the first leg, ankle, or foot of the first lower extremity;

quantifying, by the processor, a propulsion phase of a gait cycle of the lower extremity based, at least in part, on the received motion data to obtain propulsion phase characteristics of the lower extremity over the period of time;

calculating, by the processor, one or more gait characteristics based, at least in part on, the propulsion phase characteristics, the one or more gait characteristics including a propulsion efficiency of the user during the propulsion phase;

determining, by the processor, a risk level of the first or second lower extremity for one or more medical conditions based, at least in part, on:
a ratio of the propulsion efficiency to a maximum pressure of a forefoot of the first or second lower extremity during the propulsion phase, or
a ratio of the propulsion efficiency to a time integral of a pressure of the forefoot during the propulsion phase; and providing, by the processor, one or more treatment options to reduce the risk level.

2. The method of claim 1, wherein the motion data regarding motion of the first lower extremity and the second lower extremity comprises angular velocity data of the first leg of the first lower extremity or the second leg of the second lower extremity, and wherein quantifying the propulsion phase includes:

determining a stance phase of the gait cycle based, at least in part, on the motion data; and determining an initiation of the propulsion phase based on an angular velocity of the first or second leg exceeding a predetermined angular velocity following a midpoint of the stance phase and preceding a termination of the propulsion phase.

3. The method of claim 1, wherein the step of calculating the one or more gait characteristics comprises identifying the propulsion phase for a movement of the first or second lower extremity during a continuous walking bout of the user.

4. The method of claim 3, wherein quantifying the propulsion phase comprises determining a duration of the propulsion phase.

5. The method of the claim 1, wherein the one or more sensors of the first sensing device and the one or more sensors of the second sensing device are each integrated into a respective at least one of a shoe, an ankle foot orthosis, a sock, a sandal, an insole, an offloading, or a skin of a user.

6. The method of claim 1, wherein determining a risk level of the first or second lower extremity comprises determining whether the first or second lower extremity is non-frail, pre-frail, or frail.

7. The method of claim 1, wherein the one or more gait characteristics comprise at least one of:
a propulsion duration;
a propulsion acceleration;
a mid-stance speed;
a speed norm;
a toe-off speed; and
a mid-swing speed.

8. A system, comprising:
a first sensing device wearable on a first lower extremity of a user, the first sensing device comprising:
a first sensor configured to collect first motion data regarding motion of the first lower extremity over a period of time;
a first memory to store the first motion data collected by the first sensor; and
a first wireless transmitter configured to wirelessly transmit the first motion data stored in the first memory for risk level analysis of the first motion data,
wherein the first sensing device is configured to be one of: (i) integrated into a first article of clothing worn on a first leg, ankle, or foot of the first lower extremity, (ii) attached directly to a skin of the first leg, ankle, or foot of the first lower extremity via adhesive or a strap, or (iii) implanted in the first leg, ankle, or foot of the first lower extremity;
a second sensing device wearable on a second lower extremity of a user, the second sensing device comprising:
a second sensor configured to collect second motion data regarding motion of the second lower extremity over a period of time;
a second memory to store the second motion data collected by the second sensor; and
a second wireless transmitter configured to wirelessly transmit the second motion data stored in the second memory for risk level analysis of the second motion data; and
a processing station coupled to the first and second sensing devices, the processing station comprising a processor configured to perform operations comprising:
receiving, wirelessly over a network, the first and second motion data from the first and second wireless transmitters;
quantifying a propulsion phase based on the received first and second motion data to obtain propulsion phase characteristics of the first lower extremity and the second lower extremity over the period of time;
calculating one or more gait characteristics based, at least in part, from the propulsion phase characteristics, the one or more gait characteristics including a propulsion efficiency of the user during the propulsion phase;
determining a risk level of the first or second lower extremity for one or more medical conditions based, at least in part, on:
a ratio of the propulsion efficiency to a maximum pressure of a forefoot of the first or second lower extremity during the propulsion phase, or
a ratio of the propulsion efficiency to a time integral of a pressure of the forefoot during the propulsion phase; and
providing one or more treatment options to reduce the risk level.

9. The system of claim 8, wherein the first and second motion data regarding motion of the first lower extremity and the second lower extremity of the user comprises kinematic data of the first leg of the first lower extremity and the second leg of the second lower extremity.

10. The system of claim 8, wherein the step of calculating the one or more gait characteristics comprises identifying the propulsion phase for a movement of the first or second lower extremity during a continuous walking bout of the user.

11. The system of claim 10, wherein quantifying the propulsion phase comprises determining a duration of the propulsion phase.

12. The system of the claim 8, wherein each of the first sensing device and the second sensing device is integrated into a respective at least one of a shoe, an ankle foot orthoses, a sock, an insole, a sandal, an offloading, or a skin of the user.

13. The system of claim 8, wherein determining a risk level of the first lower extremity or the second lower extremity comprises determining whether the first lower extremity or the second lower extremity is non-frail, pre-frail, or frail.

14. The system of claim 8, wherein the one or more gait characteristics comprise at least one of:
   a propulsion duration;
   a propulsion acceleration;
   a mid-stance speed;
   a speed norm;
   a toe-off speed; and
   a mid-swing speed.

15. A computer program product comprising:
   a non-transitory computer readable medium comprising instructions executable by a processor to perform steps comprising:
      receiving, from one or more sensors of a first sensing device worn on a first lower extremity of a user and from one or more sensors of a second sensing device worn on a second lower extremity of the user, motion data regarding motion of the first lower extremity and the second lower extremity over a period of time, wherein:
         the first sensing device is one of: (i) integrated into a first article of clothing worn on a first leg, ankle, or foot of the first lower extremity, (ii) attached directly to a skin of the first leg, ankle, or foot of the first lower extremity via adhesive or a strap, or (iii) implanted in the first leg, ankle, or foot of the first lower extremity;

quantifying propulsion phase based on the received motion data to obtain propulsion phase characteristics of the lower extremity over the period of time;
      calculating one or more gait characteristics based, at least in part, on the propulsion phase characteristics, the one or more gait characteristics including a propulsion efficiency of the user during the propulsion phase;
      determining a risk level of the lower extremity for one or more medical conditions based, at least in part, on:
         a ratio of the propulsion efficiency to a maximum pressure of a forefoot of the lower extremity during the propulsion phase, or
         a ratio of the propulsion efficiency to a time integral of a pressure of the forefoot during the propulsion phase; and
      providing one or more treatment options to reduce the risk level.

16. The computer program product of claim 15, wherein the step of calculating the one or more gait characteristics comprises identifying the propulsion phase for a movement of the first or second lower extremity to determine the propulsion efficiency based, at least in part, on the gait characteristics from the propulsion phase characteristics.

17. The computer program product of claim 16, wherein the step of identifying the propulsion phase comprises identifying a continuous walking bout, and wherein the step of calculating one or more gait characteristics comprises calculating an exhaustion based, at least in part, on determining a reduction in the propulsion efficiency over a plurality of walking steps.

18. The method of claim 1, wherein the motion data is received while the user is located outside a controlled environment in which a trained medical professional can observe the user.

19. The method of claim 1, wherein the motion data is continuously received while the user is unobserved by a human eye.

20. The method of claim 1, wherein the motion data is received when the user is in a first geographic location and the processor is located in a second geographic location different than the first geographic location.

* * * * *